United States Patent [19]

Murai et al.

[11] 4,210,671
[45] Jul. 1, 1980

[54] ABIETAMIDE DERIVATIVES, THEIR PRODUCTION AND USE

[76] Inventors: Hiromu Murai; Katsuya Ohata; Hiroshi Enomoto; Kenji Sempuku; Koji Kitaguchi; Yukio Fujita; Yoshiaki Yoshikuni; Kohei Kura; Katsuhide Saito; Tamiki Mori; Yasuo Yasutomi, all of Kyoto, Japan

[21] Appl. No.: 576,303

[22] Filed: May 12, 1975

[30] Foreign Application Priority Data

May 17, 1974 [JP] Japan .................................. 49-55758

[51] Int. Cl.$^2$ .................... A61K 31/16; A61K 31/165
[52] U.S. Cl. ............................... 424/324; 260/557 B; 424/320
[58] Field of Search .............................. 424/320, 324; 260/557 B, 102

[56] References Cited

U.S. PATENT DOCUMENTS

| | | | |
|---|---|---|---|
| 1,986,854 | 1/1935 | Reid | 260/102 |
| 2,137,295 | 11/1938 | Koeberle | 260/102 |

OTHER PUBLICATIONS

*Organic Chemistry,* Fieser & Fieser, 3rd Ed., 1960, pp. 178, 179 & 181.

*Chemical Abstracts,* vol. 56, 10195, (1962).

*Primary Examiner*—Frederick E. Waddell

[57] ABSTRACT

A process for the preparation of amide derivatives of abietic acid, dehydroabietic acid, dihydroabietic acid or tetrahydroabietic acid which comprises reacting abietic acid, dehydroabietic acid, dihydroabietic acid or tetrahydroabietic acid or a reactive derivative thereof with an amine of the following formula:

HNRR' wherein R and R' are each hydrogen, a straight chain or branched alkyl group having 3 to 15 carbon atoms, a lower alkenyl group, a cycloalkyl group, a phenyl group, a phenylalkyl group and a phenylalkyl group having a lower alkyl group at the α-position, with the proviso that such amines where both R and R' are hydrogen or where one of R and R' is hydrogen and the other is phenyl are excluded.

The invention further comprises the resulting abietamide derivative reaction products, compositions containing effective blood serum cholesterol-reducing amounts of said abietamide derivatives and their use as anti-arteriosclerotic agents.

31 Claims, No Drawings

ABIETAMIDE DERIVATIVES, THEIR PRODUCTION AND USE

DESCRIPTION OF THE INVENTION

This invention relates to the preparation of novel compounds, namely abietic or diterpenic acid amides such as abietamides (hereinafter referred to as "AAM"), dehydroabietamides (hereinafter referred to as "DEAM"), dihydroabietamides (hereinafter referred to as "DIAM") and tetrahydroabietamides (hereinafter referred to as "TAM"). More particularly, the invention relates to a process for the preparation of diterpenic acid amides such as AAM, DEAM, DIAM and TAM by reacting a diterpenic acid such as abietic acid (hereinafter referred to as "AA"), dehydroabietic acid (hereinafter referred to as "DEA"), dihydroabietic acid (hereinafter referred to as "DIA") and tetrahydroabietic acid (hereinafter referred to as "TA") or a reactive derivative thereof such as an acid anhydride, an ester or an acid halide with an amine of the formula HNRR', wherein R and R' are each hydrogen, a straight chain or branched alkyl group having 3 to 15 carbon atoms, a lower alkenyl group, a cycloalkyl group, a phenyl group, a phenylalkyl group and a phenylalkyl group having a lower alkyl group at the α-position, with the proviso that such amines where both R and R' are hydrogen or where one of R and R' is hydrogen and the other is phenyl are excluded, thereby obtaining the corresponding diterpenic acid amides.

In practicing this reaction, a dehydrating agent represented by a dicycloalkyl-dicarboxydiimide and a basic catalyst represented by a hydroxide, alkoxide or amide of an alkali metal may be used.

These abietamides (such as AAM, DEAM, DIAM and TAM) prepared according to the process of this invention have high activity in reducing cholesterol in blood and are very valuable as anti-arteriosclerotic agents and for the treatment of mammals having hypercholesterolemia.

Diterpenic (abietic) acids useful as starting compounds of this invention are readily available. Especially AA is a naturally occurring compound which is contained in large quantitites in resins of plants belonging to the family Pinaceae and is easily available at low cost. DEA is obtained in a high yield by treating a resin of a plant of the family Pinaceae with Pd-carbon, and such Pd-carbon-treated resin containing DEA of high content can easily be obtained in the market. Further, DIA and TA can easily be obtained by reacting AA with a suitable reducing agent.

Conversion of diterpenic acids into reactive derivatives such as acid anhydrides, esters and acid halides is carried out according to conventional procedures. More specifically, acid anhydrides are generally formed by using dehydrating agents such as acetic anhydride and acetyl chloride, esters are formed by usual esterification methods represented by methylation with diazomethane, and acid halides are formed by halogenation using such halogenating agents as $PX_5$, $PX_3$ and $SOX_2$ (in which X stands for a halogen atom such as chlorine).

The amine to be used as the other reactant includes a variety of compounds represented by the above general formula NHRR'. As examples of such amines, there can be mentioned isopropylamine, decylamine, dodecylamine, penta-decylamine, allylamine, diallylamine, cyclohexylamine, cycloheptylamine, cyclopentylamine, benzylamine, α-methylbenzylamine, α-ethylbenzylamine, dibenzylamine, β-phenethylamine, N-methyl-N-cyclohexylamine, N-ethyl-N-benzylamine, N-methylaniline, N-phenyl-N-benzylamine and the like.

As solvents for the reaction, there can be employed alcohols such as methanol and ethanol, aliphatic and aromatic hydrocarbons such as n-hexane, benzene and xylene, halogenated hydrocarbons such as chloroform, cyclic ethers such as dioxane and tetrahydrofuran, and aromatic heterocyclic compounds represented by pyridine. Since the reaction frequently proceeds in the absence of a solvent, the non-solvent type of reaction can often be employed.

Starting compounds are generally charged in such amounts that 1.5 to 3 moles of the amine is used per mole of the diterpenic acid or its derivative, for example, its acid anhydride, ester or acid halide. At the charging of the starting compounds, if desired, a suitable amount of the acid component may be charged in the dissolved state or suspended in a solvent and the amine may be added little by little to the solution or suspension under cooling and agitation, if necessary.

The reaction is carried out appropriately under ice cooling, at room temperature or under heating and it is generally completed within 12 hours. Completion of the reaction can easily be confirmed by disappearance of spots of the starting substances by silica gel thin layer chromatography using a developing agent such as chloroform.

After completion of the reaction, the intended diterpenic acid amide such as AAM, DEAM, DIAM and TAM can be isolated from the reaction mixture in a manner per se known. For example, when a reaction solvent miscible with water is employed, the solvent is removed from the reaction mixture under reduced pressure and a water-immiscible solvent such as ether or benzene is added to the residue. In case a water-immiscible solvent such as benzene or n-hexane is employed, the reaction mixture is washed, according to need, with a dilute acid of a concentration of 3 to 5%, a dilute aqueous solution containing 3 to 5% of an alkali and then with water and dried, and when the solvent was removed from the washed layer, the intended product is obtained generally in the form of a crystalline powder. Recrystallization is conducted by using a suitable recrystallization solvent. In case the residue left after removal of the solvent is an oily product, purification is performed by alumina or silica gel column chromatography or preparative thin layer chromatography.

DIA used in this invention is $\Delta^8$-dihydroabietic acid, but DIA that can be employed for the synthesis of the amide is not limited to the $\Delta^8$-dihydro-compound but $\Delta^7$-, $\Delta^{13}$- and $\Delta^{14}$-isomers are intended to be included in the scope of this invention.

This invention will now be described in detail by reference to the following non-limitative Examples.

EXAMPLE 1

Preparation of N-Benzyltetrahydroabietamide

An acid chloride prepared from 3.06 g (10 millimoles) of TA and excess thionyl chloride was added to 10 ml of pyridine, and 3.22 g (30 millimoles) of benzylamine was added to the mixture under agitation and ice cooling. The mixture was agitated under ice cooling for 30 minutes. Pyridine was removed under reduced pressure and 100 ml of ether was added to the residue. The insoluble matter was removed by filtration, and the filtrate was washed with 5% HCl, water, 3% NaOH aqueous solution and water in this order. The ether layer was dried over anhydrous magnesium sulfate and filtered. Ether was removed and the residual crystalline powder was recrystallized from n-hexane to give 3.01 g of colorless needles melting at 112° to 114° C. (the yield being 76.1%).

Elementary Analysis Values as $C_{27}H_{41}ON$: Calculated: C=81.97%, H=10.51%, N=3.54%: Found: C=81.91%, H=10.56%, N=3.71%.

EXAMPLE 2

Preparation of N-Isopropyl-$\Delta^8$-Dihydroabietamide

A methyl ester prepared from 4.87 g (16 millimoles) of $\Delta^8$-DIA and excess diazomethane was added to 30 ml of xylene, and 2.90 g (48 millimoles) of isopropylamine and 1.95 g (50 millimoles) of sodium amide were added to the mixture. Then, the resulting liquid mixture was sealed in a pressure tube and heated at 180° C. for 20 hours. The reaction mixture liquid was filtered, and the filtrate was washed with 5% HCl and then with water. The xylene layer was dried over anhydrous sodium sulfate and filtered. Xylene was removed under reduced pressure and the residual crystalline powder was recrystallized from n-hexane to give 4.9 g of colorless needles having a melting point of 162° to 163° C. (the yield being 86.4%)

Elementary Analysis Values as $C_{23}H_{39}ON$: Calculated: C=79.94%, H=11.83%, N=4.05%: Found: C=80.09%, H=11.41%, N=4.34%.

EXAMPLE 3

Preparation of N-Methyl-N-Cyclohexylabietamide

A liquid mixture comprising 5.86 g (10 millimoles) of AA anhydride, 2.26 g (20 millimoles) of N-methyl-N-cyclohexylamine amine and 50 ml of xylene was heated and refluxed for 8 hours. The reaction mixture was cooled and washed with 3% KOH aqueous solution, water, 3% HCl and water in this order. The xylene layer was dried over anhydrous magnesium sulfate and filtered. Then, xylene was removed under reduced pressure, and when the oily residue was allowed to stand quiescent, crystallization occurred. Recrystallization from acetone gave 3.15 g of colorless scales melting at 130° to 131.5° C. (the yield being 79.4%).

Elementary Analysis Values as $C_{27}H_{42}ON$: Calculated: C=81.55%, H=10.90%, N=3.52%: Found: C=81.53%, H=11.10%, N=3.71%.

EXAMPLE 4

Preparation of N-Cyclohexyldehydroabietamide

A liquid mixture comprising 1.61 g (5 millimoles) of DEA, 0.66 g (6 millimoles) of cyclohexylamine, 1.24 g (6 millimoles) of dicyclohexylcarbodiimide and 20 ml of dioxane was agitated at room temperature for 6 hours, and the mixture was heated at 60° C. for 1 hour. The reaction mixture was concentrated under reduced pressure to remove dioxane, and 100 ml of methylene chloride was added to the oily residue. The methylene chloride layer was washed with 3% HCl and water, dried over anhydrous sodium sulfate and filtered. The filtrate was concentrated so that the volume was reduced to 25 ml, and the concentrate was allowed to stand quiescent at room temperature overnight. The precipitate which formed was removed by filtration, and the filtrate was concentrated to dryness. The powdery residue was recrystallized from methanol to give colorless needles melting at 188° to 189° C. (the yield being 84.6%).

Elementary Analysis Values as $C_{26}H_{39}ON$: Calculated: C=81.83%, H=10.30%, N=3.67%: Found: C=82.06%, H=10.54%, N=3.50%.

The following compounds were prepared in the same manner described in Examples 1 to 4:

N-Isopropyltetrahydroabietamide: melting at 114° to 116° C.
N-Decylabietamide: oily substance
N-Dodecylabietamide: oily substance
N-Dodecyldehydroabietamide: oily substance
N-Pentadecylabietamide: oily substance
N-Allyldihydroabietamide: melting at 92° to 94° C.
N-Allylabietamide: oily substance
N,N-Diallyldihydroabietamide: oily substance
N-Cyclohexyltetrahydroabietamide: melting at 146° to 147° C.
N-Cycloheptyldihydroabietamide: melting at 176° to 178° C.
N-Cycloheptylabietamide: melting at 146° to 148° C.
N-Cyclopentyltetrahydroabietamide: melting at 181° to 183° C.
N-Cyclopentylabietamide: melting at 164° to 165° C.
N-Benzyldihydroabietamide: melting at 125° to 126° C.
N-Benzylabietamide: melting at 106° to 107° C.
N-$\alpha$-Phenylethyltetrahydroabietamide: powdery substance
N-$\alpha$-Phenylethyldihydroabietamide: melting at 125° to 128° C.
N-$\alpha$-Phenylethylabietamide: melting at 85° to 87° C.
N-$\alpha$-Phenylethyldehydroabietamide: melting at 173° to 175° C.
N-$\alpha$-Phenylpropyldihydroabietamide: melting at 106° to 109° C.
N-$\alpha$-Phenylpropyldehydroabietamide: melting at 153° to 154° C.
N-$\alpha$-Phenylhexyldihydroabietamide: melting at 114° C. to 115° C.
N,N-Dibenzyltetrahydroabietamide: oily substance
N,N-dibenzylabietamide: oily substance
N-$\beta$-Phenylethyldihydroabietamide: glassy substance
N-Methyl-N-cyclohexyltetrahydroabietamide: glassy substance N-Ethyl-N-benzyldihydroabietamide: melting at 106° to 107.5° C.
N-Ethyl-N-benzyldehydroabietamide: melting at 124° to 125° C.
N-Methyl-N-phenyltetrahydroabietamide: melting at 105° to 107° C.
N-Methyl-N-phenyldihydroabietamide: melting at 118.8° to 119.2° C.
N-Methyl-N-phenyldehydroabietamide: melting at 109° to 110° C.
N-Phenyl-N-benzyltetrahydroabietamide: melting at 127° to 128° C.

Compounds according to this invention have high activity in reducing cholesterol in blood, which can be proved by an experiment described below, and hence are useful in the treatment of hypercholesterolemia.

A completely synthetic diet containing 1% of cholesterol, 0.25% of sodium cholate and 0.03% and 0.1% of the test compound is given to a group of 6 male rats having a body weight of about 50 g consecutively for 3 days, and the rats are fasted overnight. Then, the rats are decapitated, and their blood is collected to determine the cholesterol concentration in the collected blood. The concentration of cholesterol in blood is measured with Technicon Autoanalyzer (Technicon Laboratory: Method File N-24a). Obtained results are shown in Table 1.

Table 1

| Compound | % Inhibition Dose in Diet | |
|---|---|---|
| | 0.03% | 0.1% |
| N-Cyclopentylabietamide | 11 | 32** |
| N-Benzyldihydroabietamide | 25* | 64** |
| N-α-Phenylethyldihydroabietamide | 71** | 99** |
| N-Methyl-N-phenyldihydroabietamide | −8 | 27** |

Each value shown in the Table is a relative value determined based on the supposition that the value of the control group (the cholesterol-administered group) is 0 and the value of the normal group (the non-cholestero-administered group) is 100. The mark "*" indicates that the value is statistically significant over the control group with a significant level of 5% and the mark "**" indicates that the value is statistically significant over the control group with a significance level of 1%.

From the results shown in the Table, it will readily be understood that each compound has a significant effect of reducing cholesterol in blood of subjects having hypercholesterolemia even when it is administered in a very minute amount and is very valuable as an anti-arteriosclerotic agent. The active anti-hypercholesteremic compound or composition may be administered in any suitable or conventional manner in combination, if desired, with a pharmaceutically acceptable carrier or vehicle.

What is claimed is:

1. An amide selected from the group consisting of the N-isopropyl; N-decyl; N-dodecyl; N-pentadecyl; N-allyl; N,N-diallyl; N-cyclohexyl; N-cyclohexptyl; N-cycloentyl; N-benzyl; N-α-methylbenzyl N-α-ethylbenzyl; N,N-dibenzyl; N-β-phenethyl; N-methyl-N-cyclohexyl; N-ethyl-N-benzyl; N-methyl-N-phenyl; and N-phenyl-N-benzyl amides of a diterpenic acid selected from the group consisting of dehydroabietic acid, dihydroabietic acid and tetrahydroabietic acid.

2. An amide according to claim 1 which is N-benzyl-tetrahydroabietamide.

3. An amide according to claim 1 which is N-isopropyl-$\Delta^8$-dihydroabietamide.

4. An amide according to claim 11 which is N-cyclohexyldehydroabietamide.

5. An amide according to claim 1 which is N-isopropyltetrahydroabietamide.

6. An amide according to claim 1 which is N-dodecyldehydroabietamide.

7. An amide according to claim 1 which is N-allyldihydroabietamide.

8. An amide according to claim 1 which is N,N-diallyldihydroabietamide.

9. An amide according to claim 1 which is N-cyclohexyltetrahydroabietamide.

10. An amide according to claim 1 which is N-cycloheptyldihydroabietamide.

11. An amide according to claim 1 which is N-cyclopentyltetrahydroabietamide.

12. An amide according to claim 1 which is N-benzyldihydroabietamide.

13. An amide according to claim 1 which is N-α-phenylethyltetrahydroabietamide.

14. An amide according to claim 1 which is N-α-phenylethyldihydroabietamide.

15. An amide according to claim 1 which is N-α-phenylethyldehydroabietamide.

16. An amide according to claim 1 which is N-α-phenylpropyldihydroabietamide.

17. An amide according to claim 1 which is N-α-phenylpropyldehydroabietamide.

18. An amide according to claim 1 which is N-α-phenylhexyldihydroabietamide.

19. An amide according to claim 1 which is N,N-dibenzyltetrahydroabietamide.

20. An amide according to claim 1 which is N-β-phenylethyldihydroabietamide.

21. An amide according to claim 1 which is N-methyl-N-cyclohexyltetrahydroabietamide.

22. An amide according to claim 1 which is N-ethyl-N-benzyldihydroabietamide.

23. An amide according to claim 1 which is N-ethyl-N-benzyldehydroabietamide.

24. An amide according to claim 1 which is N-methyl-N-phenyltetrahydroabietamide.

25. An amide according to claim 1 which is N-methyl-N-phenyldihydroabietamide.

26. An amide according to claim 1 which is N-methyl-N-phenyldehydroabietamide.

27. An amide according to claim 1 which is N-phenyl-N-benzyltetrahydroabietamide.

28. An oral pharmaceutical composition useful for the lowering of blood cholesterol which comprises an antihypercholesterolemically effective amount of an amide selected from the group consisting of the N-isopropyl; N-decyl; N-dodecyl; N-pentadecyl; N-allyl; N,N-diallyl; N-cyclohexyl; N-cycloheptyl; N-cyclopentyl; N-benzyl; N-α-methylbenzyl; N-α-ethylbenzyl; N,N-dibenzyl; N-β-phenethyl; N-methyl-N-cyclohexyl; N-ethyl-N-benzyl; N-methyl-N-phenyl; and N-phenyl-N-benzyl amides of a diterpenic acid selected from the group consisting of abietic acid, dehydroabietic acid, dihydroabietic acid and tetrahydroabietic acid in combination with a pharmaceutically acceptable carrier.

29. An oral composition useful for the lowering of blood cholesterol which comprises an antihypercholesterolemically effective amount of an amide selected from the group consisting of N-benzyltetrahydroabietamide, N-isopropyl-$\Delta^8$-dihydroabietamide, N-methyl-N-cyclohexylabietamide, N-cyclohexyldehydroabietamide, N-isopropyltetrahydroabietamide, N-decylabietamide, N-dodecylabietamide, N-dodecydehydroabietamide, N-pentadecylabietamide, N-allyldihydroabietamide, N-allylabietamide, N,N-diallyldihydroabietamide, N-cyclohexyltetrahydroabietamide, N-cycloheptyldihydroabietamide, N-cycloheptylabietamide, N-cyclopentyltetrahydroabietamide, N-cyclopentylabietamide, N-benzyldihydroabietamide, N-benzylabietamide, N-α-phenylethyltetrahydroabietamide, N-α-phenylethyldihydroabietamide, N-α-phenylethylabietamide, N-α-phenylethyldehydroabietamide, N-α-phenylpropyl-dihydroabietamide, N-α-phenylpropyldehydroabietamide, N-α-phenylhexyldihydroabietamide, N,N-dibenzyltetrahydroabietamide, N,N-dibenzylabietamide, N-β-phenylethyldihydroabietamide, N-methyl-N-cyclohexyltetrahydroabietamide, N-ethyl-N-benzyldihydroabietamide, N-ethyl-N-benzyldehydroabietamide, N-methyl-N-phenyltetrahydroabietamide, N-methyl-N-phenyldihydroabietamide, N-methyl-N-phenyldehydroabietamide and N-phenyl-N-benzyltetrahydroabietamide in combination with a pharmaceutically acceptable carrier.

30. A method of lowering blood cholesterol in a subject having hypercholesterolemia which comprises administering to such subject an antihypercholesterolemically effective amount of an amide selected from the group consisting of the N-isopropyl; N-decyl; N-dodecyl; N-pentadecyl; N-allyl; N,N-diallyl; N-cyclohexyl; N-cycloheptyl; N-cyclopentyl; N-benzyl; N-α-methylbenzyl; N-α-ethylbenzyl; N,N-dibenzyl; N-β-phenethyl; N-methyl-N-cyclohexyl; N-ethyl-N-benzyl; N-methyl-N-phenyl; and N-phenyl-N-benzyl amides of a diterpenic acid selected from the group consisting of abietic acid, dehydroabietic acid, dihydroabietic acid and tetrahydroabietic acid.

31. A method of lowering blood cholesterol in a subject having hypercholesterolemia which comprises administering to such subject an antihypercholesterolemically effective amount of a composition according to claim 29.

* * * * *